United States Patent [19]

Ciurca, Jr. et al.

[11] 4,178,183

[45] Dec. 11, 1979

[54] THIAZOLYL COUPLER COMPOSITIONS AND PHOTOGRAPHIC ELEMENTS SUITED TO FORMING INTEGRAL SOUND TRACKS

[75] Inventors: Samuel J. Ciurca, Jr., Rochester; Robert G. Cameron, Spencerport; Edward J. Walsh, Pittsford, all of N.Y.

[73] Assignee: Eastman Kodak Company, Rochester, N.Y.

[21] Appl. No.: 928,621

[22] Filed: Jul. 27, 1978

[51] Int. Cl.² .......................... G03C 1/76; G03C 7/24
[52] U.S. Cl. .................................. 430/553; 430/140
[58] Field of Search ...................... 96/4, 56.3, 100, 74, 96/95

[56] References Cited

U.S. PATENT DOCUMENTS

| | | | |
|---|---|---|---|
| 2,266,452 | 12/1941 | Vittum et al. | 96/56.3 |
| 2,373,821 | 4/1945 | Frohlich et al. | 96/100 |
| 3,458,315 | 7/1969 | Loria | 96/100 N |
| 3,476,563 | 11/1969 | Loria | 96/100 |

FOREIGN PATENT DOCUMENTS

| | | | |
|---|---|---|---|
| 59838 | 8/1973 | Japan | 96/4 |
| 519208 | 3/1940 | United Kingdom | 96/100 |
| 1424454 | 2/1976 | United Kingdom | 96/100 |

OTHER PUBLICATIONS

Research Disclosure No. 13460, Jun. 1975.

*Primary Examiner*—J. Travis Brown
*Attorney, Agent, or Firm*—Carl O. Thomas

[57] ABSTRACT

Ballasted 1-hydroxy-2-naphthamide couplers which are N-substituted with a thiazolyl group that is in turn substituted with a phenyl group are disclosed as well as compositions and photographic elements containing these couplers in coupler solvents. The coupler solvent particles are comprised of a combination of a coupler solvent and the coupler capable of permitting the formation of a microcrystalline dye. Surprisingly these microcrystalline dyes exhibit a broadened absorption characteristic in the 750 to 850 nm region of the spectrum. Dye images having such absorption characteristics are particularly suited to forming integral infrared absorbing sound tracks in photographic elements, such as motion picture projection films.

19 Claims, 4 Drawing Figures

THIAZOLYL COUPLER COMPOSITIONS AND PHOTOGRAPHIC ELEMENTS SUITED TO FORMING INTEGRAL SOUND TRACKS

FIELD OF THE INVENTION

This invention relates to photographic elements and compositions adapted to form infrared absorbing dyes, particularly those useful in forming integral dye sound track motion picture films, and to couplers particularly suited for forming microcrystalline infrared absorbing dyes when dispersed in coupler solvents.

BACKGROUND OF THE INVENTION

In black-and-white motion picture projection films it is frequently desirable to provide an integral sound track. Both the photographic image and sound track images in the film are silver. The sound track, which can be of variable density or variable area, is read optically by a photocell which detects infrared radiation passing therethrough. The peak sensitivity of these photocells, generally referred to as S-1 photocells, is typically at about 800 nm plus or minus 50 nm. The wide variance in peak absorption is of little importance, since silver has a substantially uniform absorption in the infrared region of the spectrum.

In color photography, instead of employing silver images, as in black-and-white photography, the oxidized developing agent which is generated in imagewise developing silver halide to silver is used to form a dye image. The formation of color photographic images by imagewise reaction (coupling) of oxidized aromatic primary amine developing agents with incorporated color-forming couplers to form dyes is well known. In these processes, the subtractive process of color formation is ordinarily used, and the image dyes customarily formed are cyan, magenta and yellow, the colors that are complementary to the primary colors, red, green and blue, respectively. The silver image which is formed by development is an unwanted by-product which is removed by bleaching.

In color motion picture projection films it is conventional to employ a silver sound track. The requirement that silver be retained in the optical sound track of the motion picture film is distinctly disadvantageous because the developed silver must be removed from the picture area without disturbing the silver in the optical sound track. This has given rise to processing techniques which require the separate treatment of a portion of the film at least once during processing in order to obtain a silver sound track.

The desirability of employing dye sound tracks in color motion picture projection films, particularly dye sound tracks compatible with projection equipment now in use designed for films having silver sound tracks, has been long recognized. Unfortunately, the subtractive dyes which form the picture image have their regions of maximum absorption in the range of from about 400 to 700 nm and are relatively transparent in the infrared region where the S-1 photocells are most sensitive. In looking for dyes suitable for use in forming infrared absorbing sound tracks for color motion picture projection films two principal obstacles have been encountered. First, the dyes have for the most part lacked sufficient peak absorption in the required region of the spectrum. Second, the absorption peaks of the dyes have not been broad enough to accomodate the plus or minus 50 nm variation in peak sensitivity of S-1 photocells. Infrared absorbing dyes which have been disclosed for use in forming integral dye sound tracks are illustrated by Vittum et al U.S. Pat. No. 2,266,452, issued Dec. 16, 1941, and Frohlich et al U.S. Pat. No. 2,373,821, issued Apr. 17, 1945. More recent disclosures which address maximum absorption peak densities, but which do not address the breadth of the absorption peak, are illustrated by Japanese Publication No. 59838, laid open Aug. 22, 1973, based on patent application No. 94266, filed Nov. 24, 1971, and United Kingdom Pat. No. 1,424,454.

It is generally recognized that cyan dyes have at least some tail absorption in the near infrared region of the spectrum. For example, Frohlich et al, cited above, employs for near infrared absorption 1-hydroxy-2-naphthamide couplers which are N-substituted with a benzothiazole ring. Such cyan dye-forming coupler structures are also disclosed, for example, by Loria U.S. Pat. No. 3,458,315, issued July 29, 1969, and U.S. Pat. No. 3,476,563, issued Nov. 4, 1969, and Kendall et al U.K. Pat. No. 519,208. 1-hydroxy-2-naphthamide couplers useful in forming infrared absorbing sound tracks are disclosed by Ciurca, *Research Disclosure*, Vol. 134, June 1975, Item 13460, and Vol. 151, Nov. 1976, Item 15125.

BRIEF DESCRIPTION OF THE INVENTION

In one aspect, this invention is directed to a photographic element comprising a support and, coated thereon, at least one layer unit which comprises a photographic silver halide emulsion and coupler solvent particles dispersed in a photographically useful amount in the emulsion layer or in an adjacent hydrophilic colloid layer. The photographic element is characterized by the improvement wherein the coupler solvent particles are comprised of a combination, capable of permitting the formation of a microcrystalline dye, of a coupler solvent and a coupler of the formula:

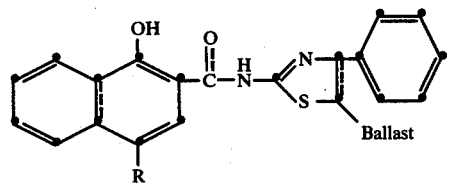

wherein R is a coupling-off group and Ballast is a hydrophobic photographic ballasting group.

In another aspect, this invention is directed to a composition, which can be coated to form a layer of a photographic element, comprising a hydrophilic colloid and coupler solvent particles dispersed therein in a photographically useful amount comprised of a combination, of permitting the formation of a microcrystalline dye, of a coupler solvent and a coupler of the formula

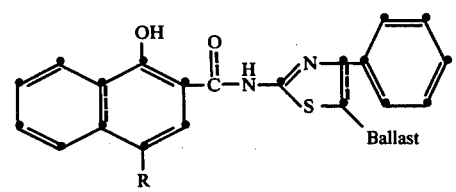

wherein R is a coupling-off group and Ballast in a hydrophobic photographic ballasting group.

In still another aspect, this invention is directed to a photographically useful dye-forming coupler capable of forming a dye having an absorption peak in the infrared portion of the spectrum of the formula

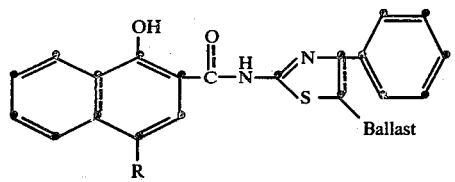

wherein R is a coupling-off group and Ballast is a hydrophobic photographic ballasting group.

It is a surprising feature of this invention that the microcrystalline dyes which can be formed with coupler-coupler solvent combinations have absorption peaks in the infrared portion of the spectrum and which, when incorporated in a photographic element, are capable of producing densities at 800 nm well above 1.0. It is still more surprising that broad absorption peaks can be produced in the 800 nm region of the spectrum. Particularly, it is surprising that these coupler-coupler solvent combinations can produce infrared absorbing dye images having sufficient peak densities and spectral peak breadth to be useful in modulating the response of an S-1 photocell when coated in a photographic element to form a sound track. The present invention offers the specific advantage of permitting color motion picture projection films to be formed with integral infrared absorbing dye sound tracks, thereby eliminating the disadvantages in processing of selectively retaining silver in sound track areas and offering the distinct advantage of allowing such integral infrared absorbing dye sound track color motion picture films to be employed in projection equipment having S-1 and similar photocells intended for modulation with a silver sound track.

DESCRIPTION OF THE PREFERRED EMBODIMENTS

Figure 1:
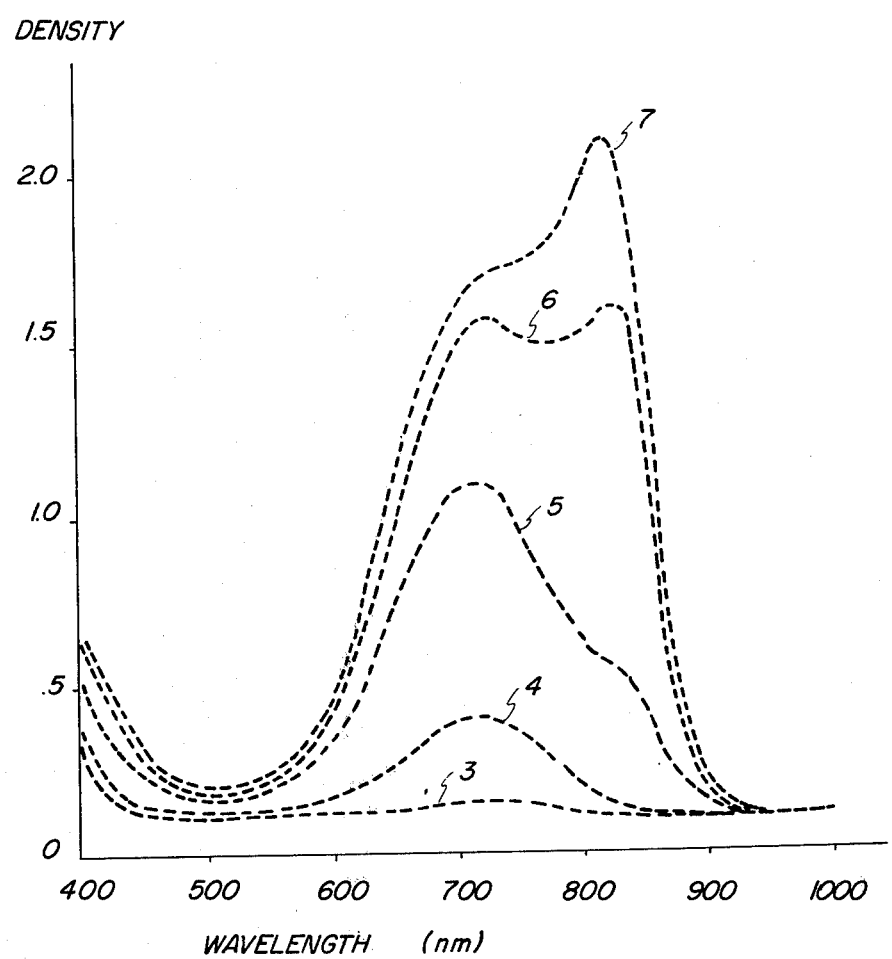
FIGS. 1 through 4 show dye absorption curves produced by plotting density on an ordinate versus wavelength as an abscissa.

The couplers capable of reacting in a coupler solvent particle with an oxidized color developing agent to form a microcrystalline infrared absorbing dye can be chosen from among N-thiazolyl-1-hydroxy-2-naphthamides of the following formula:

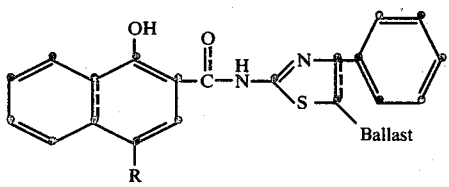

wherein
R is a coupling-off group and
Ballast is a hydrophobic photographic ballasting group.

Coupling-off groups, represented by R, are well known to those skilled in the art. Such groups are displaced when the coupler reacts with oxidized color developing agent. Thus, the coupling-off group is not included in the dye formed by this reaction. The coupling-off group can perform useful photographic functions, such as determining the equivalency of the coupler (e.g., determining if the coupler is a two-equivalent or a four-equivalent coupler), modifying the reactivity of the coupler or releasing a photographically useful fragment which can modulate other characteristics, such as inhibiting or accelerating bleaching, inhibiting development, color correction and the like. Representative of useful conventional coupling-off groups are hydrogen, alkoxy, aryloxy, arylazo, thioether and heterocyclic groups, such as oxazolyl, diazolyl, triazolyl and tetrazolyl groups. Hydrogen is a preferred coupling-off group.

Ballast in the general formula above can be chosen from conventional hydrophobic photographic ballasting groups. Such groups inhibit the diffusion of the couplers when incorporated in a hydrophilic colloid layer of a photographic element. Typical useful ballast groups include long-chain alkyl radicals linked directly or indirectly to the compound as well as aromatic radicals of the benzene and naphthylene series. Such ballast groups commonly have at least 8 carbon atoms, such as substituted or unsubstituted alkyl groups of from 8 to about 22 carbon atoms, amide radicals having 8 to 30 carbon atoms and keto radicals having 8 to 30 carbon atoms. The preferred ballast groups are the straight-chain alkyl radicals having 10 to 20 carbon atoms, optionally 12 to 16 carbon atoms.

The couplers can be chemically synthesized by techniques well known to those skilled in the art. For example, the synthesis of 1-hydroxy-N-(2-phenyl-3-tetradecylthiazolyl)-2-naphthamide set forth below can be readily adapted to the synthesis of other of the novel couplers merely by varying the substituents in the starting materials which provide the coupling-off and/or ballast groups.

The preferred coupler solvents contemplated for use in combination with the above couplers can be represented by the following formula:

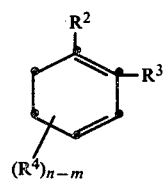

wherein
$R^2$ is a polar group,
$R^3$ is

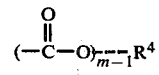

$R^4$ is alkyl of from 1 to 6 carbon atoms,
m is 1 or 2 and
n is 2, 3 or 4.

The polar group $R^2$ can be chosen from among a variety of known polar groups conventionally incorporated in photographic addenda, such as a hydroxy, an aldehyde, a ketone, an acid or acid salt, an ester, an amide, a hydroxyalkylamine, an alkoxy, an alkylthio or similar group. In a preferred form the polar group is hydroxy or an ester group, which in a specifically preferred form is identical to the group $R^3$ in its ester form. $R^4$ can be an alkyl group, such as methyl, ethyl or any one of the various isomeric forms of propyl, butyl, amyl and hexyl groups.

The following are exemplary of preferred coupler solvents contemplated for use:
  dimethyl phthalate
  diethyl phthalate
  di-n-butyl phthalate
  di-i-amyl phthalate
  n-butyl 2-methoxybenzoate
  n-amyl phthalate
  2,4-di-n-amylphenol
  2,4-di-tert-amylphenol Other conventional coupler solvents which are capable of permitting associated ballasted N-thiazolyl-1-hydroxy-2-naphthamides, described above, to form microcrystalline dyes can be employed. Coupler to coupler solvent weight ratios of from 5:1 to 1:2 can be selected. A preferred range of weight ratios is from 4:1 to 1:1, with the optimum being from about 2.5:1 to 1.5:1 for the preferred coupler solvents.

Coupler solvents of the type described above and techniques for dissolving couplers therein are known to those skilled in the art. Techniques are also well known for dispersing coupler-containing coupler solvents in hydrophilic colloid-containing coating compositions useful in forming photographic elements. The coupler-containing coupler solvent is typically dispersed in the hydrophilic colloid-containing coating composition in the form of particles of relatively small size, typically from about 0.3 to about 3.0 microns in mean diameter, usually by colloid milling. The coupler solvents herein employed, the dispersion of couplers therein, the introduction of the coupler-containing coupler solvents into hydrophilic colloid-containing coating compositions and the coating of the composition to form layers in photographic elements, are illustrated by Mannes et al U.S. Pat. No. 2,304,940, issued Dec. 15, 1942; Jelley et al U.S. Pat. No. 2,322,027, issued June 15, 1943; Vittum et al U.S. Pat. No. 2,801,170, issued July 30, 1957; Fierke et al U.S. Pat. No. 2,801,171, issued July 30, 1957; Thirtle et al U.S. Pat. No. 2,835,579, issued May 20, 1958; and Julian U.S. Pat. No. 2,949,360, issued Aug. 16, 1960, as well as the Japanese Publication No. 59838 and U.K. Pat. No. 1,424,454, both cited above, the disclosures of each of the above here being incorporated by reference.

In a simple form the photographic elements of this invention are comprised of a photographic support having coated thereon a single layer unit which comprises a photographic silver halide emulsion containing therein in a photographically useful amount particles which are comprised of the coupler and coupler solvent combined in the weight ratio described above. In a variant form, well known in the art, instead of incorporating the coupler-containing coupler solvent particles directly in the silver halide emulsion layer, the particles can be dispersed in a hydrophilic colloid layer immediately adjacent to the silver halide emulsion layer. In this form the hydrophilic colloid layer containing the particles and the silver halide emulsion layer together form the layer unit.

Such a single layer unit element can be employed for the sole purpose of forming a sound track or, preferably, the element can be employed to form both a photographic image and a sound track. It is possible with such an element to form an infrared absorbing dye sound track and a silver photographic image or, alternatively, a silver sound track and an infrared absorbing photographic dye image. In a specifically preferred use an integral dye sound track is formed. As employed herein, the term "integral sound track" indicates that a sound track and a photographic image are formed in separate portions of the same element and that following exposure the separate areas are concurrently and identically processed (i.e., requiring no process steps other than those required for processing the photographic image portion) to form sound track and photographic records, respectively. Since the novel couplers employed in the practice of this invention produce dyes which absorb not only in the infrared, but also in the visible portion of the spectrum, both a sound track and a photographic image can be formed solely by the dye. For example, an integral sound track and photographic image can be formed by the dye, the sound track portion being read by an S-1 or similar infrared responsive photocell and the photographic image being read by the eye as a projected dye image. Other variant uses will readily occur to those skilled in the art.

In a form capable of recording multicolor images the photographic element contains in addition to the support and the single layer unit described above at least two additional layer units, and the photographic element is capable of producing multicolor photographic images. The single layer unit described above can contain a red-sensitized silver halide emulsion and be employed to form a cyan dye image as well as an infrared absorbing dye image. The same dye can form both the cyan and the infrared absorbing dye image, but it is preferred in that instance that the single layer unit described above be modified to include in addition a conventional cyan dye-forming coupler. The cyan dye-forming coupler is preferably dispersed in separate coupler solvent particles from those containing the infrared absorbing dye-forming coupler or coated without employing a coupler solvent. A second layer unit is present containing a blue-sensitive silver halide emulsion and a yellow dye-forming coupler, and a third layer unit is present containing a green-sensitized silver halide emulsion and a magenta dye-forming coupler. The construction of the second and third layer units and their relationship to the first layer unit is conventional and requires no detailed description.

In another form, which is specifically preferred, the photographic element is provided with four separate layer units. Three layer units are conventional cyan, magenta and yellow dye-forming layer units of the type found in conventional silver halide photographic elements intended to form multicolor dye images. The fourth layer unit can be identical to the single layer unit described above. in a preferred form the silver halide emulsion in the fourth layer unit is sensitized to a portion of the spectrum to which the remaining layers are relatively insensitive. For example, the fourth layer unit emulsion can be spectrally sensitized to the infrared portion of the spectrum or to portions of the visible spectrum which lie at the fringes of the spectral regions the remaining layer units are intended to record. The blue portion of the spectrum is nominally defined as from 400 to 500 nm, the green portion of the spectrum from 500 to 600 nm and the red portion of the spectrum from 600 to 700 nm. The spectral regions in the vicinity of about 500 nm and 600 nm are frequently relatively insensitive to light as compared to the mid-regions of the blue, green and red portions of the spectrum. This is done intentionally to avoid recording in a layer unit light exposure from one of the two remaining thirds of the visible spectrum. By spectrally sensitizing the emulsion of the fourth layer unit to a peak sensitivity in a region of the spectrum where the silver halide emulsions of the other three layer units are relatively insensitive, for instance at about 470 to 500 nm, the fourth layer unit can be exposed by light in this region of the spectrum to form a sound track. In one preferred form the fourth layer unit is spectrally sensitized to the infrared portion of the spectrum. The fourth layer unit can be coated in any convenient order with respect to the remaining layer units, but it is preferable to coat the fourth layer unit nearer the exposure light source than the remaining layer units, typically to overcoat the other three layer units, so that the best possible definition of the sound track image will be produced. Useful layer arrangements are disclosed in Japanese Publication No. 59838 and U.K. Pat. No. 1,424,454, cited above.

Still other variant forms of the photographic elements can be employed. For example, the emulsion of the sound track layer unit can be employed with only its native spectral sensitivity. In this instance the response of the sound track layer unit is confined to exposure to ultraviolet and the adjacent blue portion of the spectrum, the blue response varying to some extent with the slver halide chosen. In still another variant form the speed rather than the spectral response of the sound track recording layer unit can be different from that of another, image-forming layer unit. The sound track recording layer unit can be either faster or slower than an image-forming layer unit of similar spectral response. A combination of both differing spectral response and speed can also be employed to allow selective exposure of the sound track and image-forming layer units.

While any photographically useful amount of particles of the infrared absorbing dye-forming coupler and coupler solvent can be present in the layer units described above, for sound track applications employing S-1 photocells it is preferred that these particles be present in a concentration sufficient to provide a maximum dye density of at least 1.0 over the spectral region of from 750 to 850 nm, preferably at least 2. Such dye densities can be obtained readily with the preferred coupler-coupler solvent combinations within the concentration ranges conventionally employed for coupler solvent particles containing cyan, magenta and yellow dye-forming couplers. Generally coupler concentrations ranging from about 0.40 to 1.30 grams per square meter are contemplated, preferably from about 0.65 to 1.05 grams per square meter, optimally from about 0.75 to 0.95 gram per square meter.

The photographic silver halide emulsion layers, the adjacent hydrophilic colloid-containing layers in which the infrared absorbing dye-forming couplers can be incorporated and other layers, including overcoat, subbing and interlayer coatings of conventional character, can contain various colloids alone or in combination as vehicles. Suitable hydrophilic vehicle materials include both naturally-occurring substances such as proteins, for example, gelatin, gelatin derivatives, cellulose derivatives, polysaccharides such as dextran, gum arabic and the like; and synthetic polymeric substances such as water soluble polyvinyl compounds like poly(vinylpyrrolidone), acrylamide polymers and the like.

Photographic emulsion layers and other layers of photographic elements such as overcoat layers, interlayers and subbing layers, as well as receiving layers in image transfer elements can also contain alone or in combination with hydrophilic, water-permeable colloids, other synthetic polymeric vehicle compounds such as dispersed vinyl compounds such as in latex form and particularly those which increase the dimensional stability of the photographic materials. Typically synthetic polymers include those described in Nottorf U.S. Pat. No. 3,142,568 issued July 28, 1964; White U.S. Pat. No. 3,193,386 issued July 6, 1965; Houck et al U.S. Pat. No. 3,062,674 issued Nov. 6, 1962; Houck et al U.S. Pat. No. 3,220,844 issued Nov. 30, 1965; Ream et al U.S. Pat. No. 3,287,289 issued Nov. 22, 1966; and Dykstra U.S. Pat. No. 3,411,911 issued Nov. 19, 1968. Other vehicle materials include those water-soluble polymers of alkyl acrylates and methacrylates, acrylic acid, sulfoalkyl acrylates or methacrylates, those which have cross-linking sites which facilitate hardening or curing as described in Smith U.S. Pat. No. 3,488,708 issued Jan. 6, 1970, and those having recurring sulfobetaine units as described in Dykstra Canadian Pat. No. 774,054.

The vehicles and binders are typically coated from aqueous dispersions. The preferred hydrophilic colloids for coating purposes are gelatin and related derivatives. Gelatin and gelatin derivatives are typically coated in a concentration of from about 0.1 to 10 percent, preferably 2 to 6 percent, by weight, dry, based on total weight. The other hydrophilic colloids can be coated in similar concentration levels.

The silver halide photographic emulsions employed can be of any conventional, convenient form. For example, the silver halide emulsion types set forth in Paragraph I, *Product Licensing Index*, Vol. 92, December 1971, Item 9232, can be employed. The emulsions can be washed as described in Paragraph II, chemically sensitized, as described in Paragraph III and/or spectrally sensitized, as described in Paragraph XV. The emulsion and other hydrophilic colloid-containing layers of the photographic elements can contain development modifiers, as described in Paragraph IV, antifoggants and stabilizers, as described in Paragraph V, developing agents, as described in Paragraph VI, hardeners, as described in Paragraph VII, plasticizers and lubricants, as described in Paragraph XI, coating aids, as described in Paragraph XII, matting agents, as described in Paragraph XIII, brighteners, as described in Paragraph XIV, and absorbing and filter dyes, as described in Paragraph XVI. The various addenda can be incorporated by known methods of addition, as described in Paragraph XVII. The photographic elements can contain antistatic layers, as set forth in Paragraph IX. The color-forming materials, particularly the dye-forming couplers, can be chosen from those illustrated by Paragraph XXII. The dye-forming couplers which form the dye image to be viewed need not be coated in a coupler solvent, but can be coated in any conventional manner illustrated by the patents in Paragraph XVIII. As these patents further illustrate, interlayers can be provided between adjacent layer units containing compounds such as ballasted hydroquinones to prevent migration out of the layer unit of oxidized developing agent. Coating of the various materials can be undertaken employing procedures such as those described in Paragraph XVIII. *Product Licensing Index* is published by Industrial Opportunities Ltd., Homewell, Havant Hampshire, PO9 1EF, UK.

The silver halide emulsion and remaining layers of the photographic elements can be coated on any conventional photographic support. For projection film applications including an integral sound track the support is specularly transmissive—e.g., transparent. For such applications conventional photographic film supports can be employed, such as cellulose nitrate film, cellulose acetate film, poly(vinyl acetal) film, polystyrene film, poly(ethylene terephthalate) film, polycarbonate film and similar resinous film supports.

In one preferred mode of exposure the photographic element is panchromatically exposed and an edge portion of the film is exposed to infrared radiation to form the sound track. When this mode of exposure is undertaken, the silver halide grains in the sound track recording layer unit are spectrally sensitized with infrared absorbing spectral sensitizing dyes. Typical useful infrared spectral sensitizing dyes are described, for example, in Trivelli et al U.S. Pat. No. 2,245,236, issued June 10, 1941; Brooker U.S. Pat. Nos. 2,095,854 and 2,095,856 issued Oct. 12, 1937; Dieterle U.S. Pat. No. 2,084,436, issued June 22, 1937; Zeh U.S. Pat. No. 2,104,064, issued Jan. 4, 1938; Konig U.S. Pat. No. 2,199,542, issued May 7, 1940; Brooker et al U.S. Pat. No. 2,213,238, issued Sept. 3, 1940; Heseltine U.S. Pat. Nos. 2,734,900 and 3,582,344, issued Feb. 14, 1956 and June 1, 1971, respectively; Barth et al U.S. Pat. No. 2,134,546, issued Oct. 25, 1938; Brooker U.S. Pat. No. 2,186,624, issued Jan. 9, 1940; Schneider U.S. Pat. No. 2,073,759, issued Mar. 16, 1937; Thompson U.S. Pat. No. 2,611,695, issued Sept. 23, 1952; Brooker et al U.S. Pat. No. 2,955,939, issued Oct. 11, 1960; Jenkins et al U.S. Pat. No. 3,573,921, issued Apr. 6, 1971; Jeffreys U.S. Pat. No. 3,552,974, issued Jan. 5, 1971; and Fumia et al U.S. Pat. Nos. 3,482,978, 3,623,881 and 3,652,288, issued Dec. 9, 1969, Nov. 30, 1971 and Mar. 28, 1972, respectively.

The photographic elements can be processed to form dye images which correspond to or are reversals of the silver halide rendered selectively developable by image-wise exposure by conventional techniques. Multicolor reversal dye images can be formed in photographic elements having differentially spectrally sensitized silver halide layers by black-and-white development followed by a single color development step, as illustrated by the Kodak Ektachrome E4 and E6 and Agfa processes described in *British Journal of Photography Annual*, 1977, pp. 194–197, and *British Journal of Photography*, pp. 668–669. The photographic elements can be adapted for direct color reversal processing (i.e., production of reversal color images without prior black-and-white development), as illustrated by Barr U.S. Pat. No. 3,243,294; Hendess et al U.S. Pat. No. 3,647,452; Puschel et al U.S. Pat. Nos. 3,457,077 and 3,467,520 and German OLS No. 1,257,570; Accary-Venet U.K. Pat. No. 1,132,736; Schranz et al German OLS No. 1,259,700; Marx et al German OLS No. 1,259,701; Muller-Bore German OLS No. 2,005,091 and U.K. Pat. No. 1,075,385.

Multicolor dye images which correspond to the silver halide rendered selectively developable by image-wise exposure, typically negative dye images, can be produced by processing, as illustrated by the Kodacolor C-22, the Kodak Flexicolor C-41 and the Agfa color processes described in *British Journal of Photography Annual*, 1977, pp. 201–205. The photographic elements can also be processed by the Kodak Ektaprint-3 and -300 processes as described in Kodak Color Dataguide, 5th Ed., 1975, pp. 18–19, and the Agfa color process as described in *British Journal of Photography Annual*, 1977, pp. 205–206.

The photographic elements can be processed in the presence of reducible species, such as transition metal ion complexes (e.g. cobalt(III) and ruthenium(III) complexes containing amine and/or ammine ligands) and peroxy compounds (e.g. hydrogen peroxide and alkali metal perborates and percarbonates).

Dye images can be formed or amplified by processes which employ in combination with a dye-image-generating reducing agent an inert transition metal ion complex oxidizing agent, as illustrated by Bissonette U.S. Pat. Nos. 3,748,138, 3,826,652, 3,862,842 and 3,989,526 and Travis U.S. Pat. No. 3,765,891, and/or a peroxide oxidizing agent, as illustrated by Matejec U.S. Pat. No. 3,674,490, *Research Disclosure*, Vol. 116, December 1973, Item 11660, and Bissonette, *Research Disclosure*, Vol. 148, August 1976, Items 14836, 14846 and 14847. The photographic elements can be particularly adapted to form dye images by such processes, as illustrated by Dunn et al U.S. Pat. No. 3,822,129; Bissonette U.S. Pat. Nos. 3,834,907, 3,847,619 and 3,902,905 and Mowrey U.S. Pat. No. 3,904,413.

In a specific preferred application the photographic elements of this invention are employed to form a motion picture film for projection containing an integral sound track useful in a projector having an S-1 photocell. The photographic element is comprised of a transparent film support on which are coated, in the order recited, a red-sensitized cyan dye-forming coupler containing first layer unit, a green-sensitized magenta dye-forming coupler containing a second layer unit, a blue-sensitive yellow dye-forming coupler containing third layer unit and an infrared-sensitized fourth layer unit containing coupler solvent particles according to this invention, as has been described above. The picture recording portion of the element is flashed to infrared and is then exposed to the blue, green and red portions of the spectrum through a master image film. The master image film has a transparent support and has been processed so that it carries a positive multicolor dye image. The edge of the photographic element on which the integral sound track is to be formed is panchromatically exposed through a positive sound track master by a light source to which at least the fourth layer unit is sensitive. In a preferred form this is a white light source which exposes the red-sensitized, green-sensitized and blue-sensitive layer units. The fourth layer unit by reason of its native sensitivity to blue light is also exposed by the white light source. The white light source can also emit infrared to expose the fourth layer unit. The photographic element after exposure of both the picture and sound track areas is reversal processed. In reversal processing of negative-working silver halide emulsions, positive dye images are formed in unexposed areas. Since the picture area was uniformly flashed to infrared, no density attributable to the fourth layer unit is present in the picture area. In the sound track area the major portion of the infrared density is attributable to the fourth layer unit, but the other layer units can also add to the total infrared density.

In another specific application which further illustrates the diversity of uses contemplated, a motion picture projection film containing an integral sound track can also be obtained using a fourth layer unit which is spectrally sensitized to the region of 470 to 500 nm. The element can be exposed in picture recording areas through a multicolor negative master image film with red, green and blue (420 to 470 nm) light. The film sound track area can be exposed through a negative master sound track using a light source emitting in at least the 470 to 500 nm region of the spectrum. Using negative-working silver halide emulsion in the layer units, development produces in picture and sound track areas of the element positive dye images. The sound track image is formed primarily by the fourth layer unit.

In processing to form dye images in the manner described above any conventional color developing agent can be employed which will permit the formation of a microcrystalline dye. Depending upon the specific color developing agent selected, the maximum dye densities, the wavelength of the peak densities and the increased breadth of bathochromic absorption will vary. The color developing agent 4-amino-3-methyl-N-β-(methanesulfonamide)ethylaniline sulfate hydrate has been observed to produce microcrystalline infrared absorbing dye images having a maximum density in excess of 1.0, often in excess in of 2.0, not only at 800 nm, but over the entire spectral region of from about 750 to 850 nm. Such microcrystalline infrared absorbing dye images are ideally suited to forming dye sound tracks for use in motion picture projection film equipment employing S-1 and similar photocells intended to respond to silver sound tracks. In the photographic elements of this invention can be produced infrared absorbing dye sound tracks which are comparable in fidelity with the silver sound tracks they are intended to replace, although a somewhat higher gain may be required for comparable decibel output, since the dye sound track is of somewhat lower maximum density than are silver sound tracks.

As employed herein, the term "microcrystalline dye" refers to a dye which is present in a crystalline physical form, but the size of the dye crystals are too small to be visually detected with the unaided eye. Such crystals can sometimes be seen upon microscopic examination, but in many instances the crystals are of submicroscopic sizes. Since each dye is a reaction product of a coupler and an oxidized color developing agent in a coupler solvent particle, it follows that the steric configuration of the coupler, the developing agent and the coupler solvent as well as their relative proportions all influence the crystallinity of the dye produced. The choice of the coupler is generally most important to forming photographic elements which can form microcrystalline dyes. The formation of mixed phases of microcrystalline and noncrystalline dyes is specifically contemplated and is in many instances preferred to permit the formation of broadened absorption peaks. It is believed that the broadening of the absorption peak is the product of two unresolved or fused absorption peaks—one attributable to the microcrystalline dye produced and the other attributable to the noncrystalline dye produced. Although at least a portion of the dye produced is microcrystalline, it should be noted that the couplers are not themselves crystalline, since crystallinity in couplers produces significant loss of dye density attributable to lack of availability of the coupler as well as severe problems in dispersing and coating the crystalline coupler.

Crystallinity, particularly submicroscopic microcrystallinity, can be ascertained by a number of known general analytical techniques as well as by some techniques which are peculiar to the photographic arts. In photography microcrystalline dyes are commonly associated with shifts in hue as a function of concentration and by asymmetrical absorption peaks. Both hypsochromic and bathochromic shifts attributable to microcrystallinity have been observed in varied conventional dye structures. Microcrystalline dyes have, for example, found applications in photographic elements because of their sharp transition between high peak and low toe densities, as illustrated by S. J. Ciurca, *Research Disclosure*, Vol. 157, May 1977, Item 15730. Analytical techniques, such as X-ray diffraction and detection of birefringence, can also be employed to identify crystalline structure. Such analytical techniques are described by A. Weissberger and B. W. Rossiter, *Techniques of Chemistry, Physical Methods of Chemistry*, Vol. 1, p. 3A-D, Wiley, 1972.

EXAMPLES

The practice of this invention can be better appreciated by reference to the following examples:

EXAMPLE 1

A. A sample of 1-hydroxy-N-(2-phenyl-3-tetradecyl-thiazolyl)-2-naphthamide, hereinafter designated Coupler 1, used in subsequent examples, was prepared in the following manner:

In a round bottom flask were combined 25 grams (approx. 0.1 mole) of 2-amino-4-phenyl-5-n-tetradecyl-thiazole and 30 grams (approx. 0.1 mole) of phenyl 1-hydroxy-2-naphthoate. The mixture was heated at 150° to 170° C. for 3 hours. Aspirator vacuum was applied for 1 hour to facilitate removal of phenol. The hot viscous residue was poured into methanol in a 500 ml flask and stirred. The solids which precipitated were collected and recrystallized from methanol twice, providing 4 grams of crystalline solid, m.p. 51°-54° C.

B. In an alternate preparation approach, which produces Coupler 1 in association with acetic acid, the same starting materials in the round bottom flask are employed, but the mixture was heated to 140° to 145° C. for about 2 hours using an oil bath. Aspirator vacuum was then applied and heating was continued at 110° to 130° C. for 3 to 4 hours to facilitate removal of phenol. Methanol was added to the residue. After brief stirring the solution was allowed to cool slowly. The solids which formed were collected and recrystallized from methanol. Yellow needles grew in the solution but a dark material formed in the bottom of the flask. The yellow crystals were collected, then dried under vacuum overnight. Upon exposure to air for a few hours the crystals began to shrink and finally collapsed to a gum. This was recrystallized from hot acetic acid, and the product thoroughly dried, providing 11.7 grams of white fluffy needles, m.p. 73° to 74° C.

EXAMPLE 2

A. A photographic element having a transparent film support and a gelatino-silver halide emulsion layer and a clear gelatin overcoat layer coated thereon was prepared. The emulsion coating contained the ingredients set forth below in Table I. Unless otherwise stated, all coating coverages in the examples are reported parenthetically in terms of grams per square meter. Silver halide coverages are reported in terms of silver.

Table I

| Photographic Element 2-A |
|---|
| Overcoat Layer: Gelatin (0.54) |
| Gelatino-Silver Halide Emulsion Layer: |
| Infrared Sensitized Silver Halide (0.756); |
| Gelatin (2.16); Coupler 1 (0.864); |

Table I-continued

Photographic Element 2-A

Coupler Solvent Di-n-butyl phthalate (0.864)
Transparent Film Support

The coupler was dispersed in the coupler solvent which was in turn dispersed in particulate form in the gelatin of the silver halide emulsion.

B. A sample of the photographic element was exposed for 1 second at a color temperature of 2854° K. with an Eastman 1B sensitometer through a graduated density step object. The test object had 21 equal density steps ranging from 0 density at Step 1 to a density of 6.0 at Step 21.

C. The exposed sample of the photographic element was then processed at 38° C. in the following manner:

The sample was developed for 2 minutes in the black-and-white developer set forth in Table II.

Table II

Black-and-White Developer

| | |
|---|---|
| 800 ml | Water |
| 2.0 g | Sodium tetraphosphate |
| 8.0 g | Sodium bisulfite |
| 47 g | Sodium sulfite |
| 33 g | Sodium carbonate |
| 5.5 g | Hydroquinone |
| 0.35 g | 1-Phenyl-3-pyrazolidone |
| 1.3 g | Sodium bromide |
| 1.38 g | Sodium thiocyanate |
| 33 mg | Potassium iodide |
| 1.1 g | Sodium hydroxide |
| | Water to 1 liter |

The sample was then rinsed for 1 minute in a dilute acetic acid bath of the composition set forth in Table III.

Table III

Rinse Bath

| | |
|---|---|
| 800 ml | Water |
| 30 ml | Glacial Acetic Acid |
| 5.35 g | Sodium hydroxide |
| | Water to 1 liter |

The sample was then washed for 1 minute in water and immersed for 2 minutes in a reversal bath of the composition set forth in Table IV.

Table IV

Reversal Bath

| | |
|---|---|
| 1.6 ml | Propionic acid |
| 0.024 g | p-Phenylenediamine |
| 0.8 g | Stannous Chloride |
| 12 ml | Sodium hexametaphosphate |
| 2.08 ml | 7N Sulfuric acid |
| | Water to 1 liter |

The sample was then developed for 4 minutes in a color developer of the composition set forth in Table V.

Table V

Color Developer

| | |
|---|---|
| 50 g | Sodium carbonate |
| 5.0 g | Sodium sulfite |
| 1.0 g | Potassium bromide |
| 3.0 g | Sodium hexametaphosphate |
| 10.0 g | 4-Amino-3-methyl-N-ethyl-N-$\beta$-(methanesulfonamido)ethylaniline sulfate hydrate |

Table V-continued

Color Developer

| | |
|---|---|
| | Water to 1 liter |

The sample was then rinsed again for 1 minute in the rinse bath of Table III, rinsed again for 1 minute in water and then immersed for 2 minutes in a bleach bath of the composition set forth in Table VI.

Table VI

Bleach Bath

| | |
|---|---|
| 800 ml | Water |
| 1.0 g | Sodium hexametaphosphate |
| 144 g | Potassium Ferricyanide |
| 34.4 g | Sodium bromide |
| 120 g | Sodium sulfate |
| 3 ml | 50% Carbowax 1540 solution |
| 0.05 g | Sodium hydroxide |
| | Water to 1 liter |

Following bleaching the sample was immersed for 2 minutes in a fix bath of the composition set forth in Table VII.

Table VII

Fix Bath

| | |
|---|---|
| 800 ml | Water |
| 180 g | Sodium thiosulfate |
| 9 g | Sodium sulfite |
| | Water to 1 liter |

The sample was then washed for 2 minutes with water and then immersed for 30 minutes in stabilizer bath of the composition set forth in Table VIII. After removal from the stabilizer bath the element sample was allowed to dry.

VIII

Stabilizer Bath

| | |
|---|---|
| 3.0 ml | 35–40% Formaldehyde Solution |
| 10.0 ml | 10% Wetting Agent Solution |
| | Water to 1 liter |

D. In FIG. 1 a plot of density versus wavelength is shown. The reference numerals applied to the curves refer to the step number of the step tablet through which that portion of the sample was exposed. It can be seen that where low maximum dye densities were produced the absorption peak produced by the dye was in the vicinity of about 725 nm and of relatively narrow breadth. By the time the peak dye density had reached a maximum value of about 1 a broadening of the absorption peak was clearly in evidence. In Curve 6 two distinct absorption peaks are in evidence which are fused to provide a broad composite peak in excess of 1.5 in density over the spectrally region of from about 725 to 850 nm. Curve 7 shows a further extension of this trend as still higher peak dye density is attained.

Figure 2:
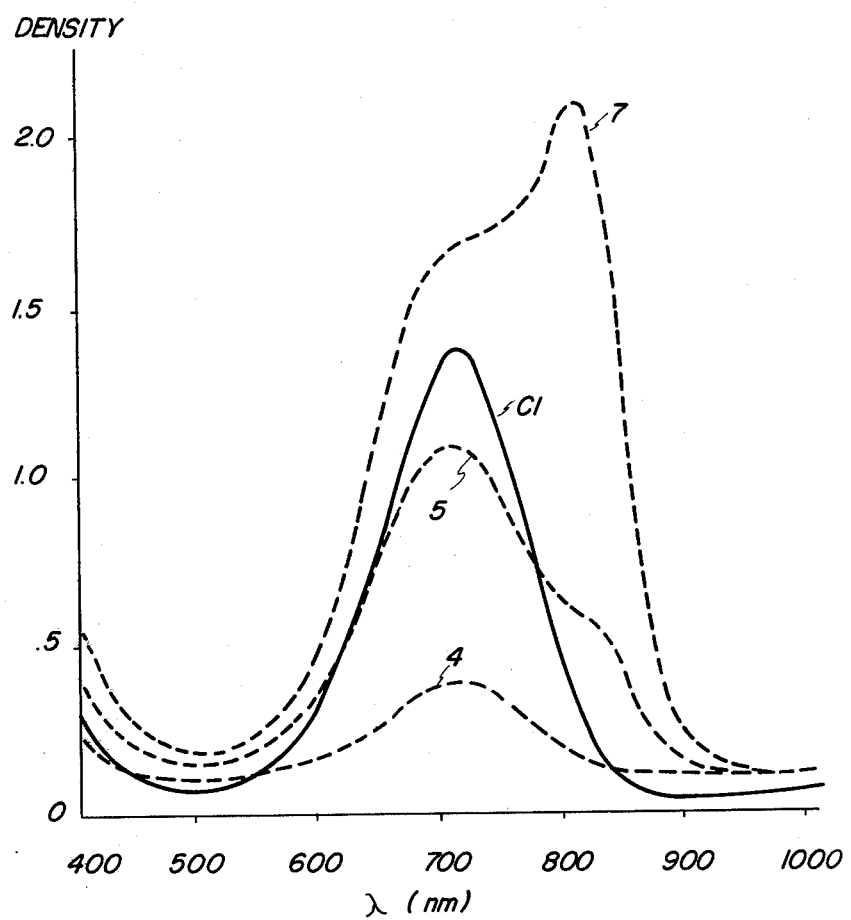

E. To observe the characteristics of the dye appart from the photographic element sample in which it was observed a portion of the dye was extracted from the sample with methanol. FIG. 2 is a plot similar to FIG. 1. Curve C1 illustrates the absorption characteristic of the dye extracted. The absorption peak of the dye is about 715 nm. Although the dye is present in a greater peak density than in Curve 5, there is no observed broadening of the absorption peak. From this comparison it is concluded that the broadened absorption peak observed is a function not separately attributable to the dye alone, but also a function of its microcrystalline form within the element sample. Curves 4, 5 and 7 in FIG. 2 are identical to Curves 4, 5 and 7 in FIG. 1 and are provided for purposes of comparison.

F. When the procedure described above in paragraphs B, C and D was repeated with a second sample, but with the substitution of the color developing agent employed therein with the color developing agent 4-amino-3-methyl-N-ethyl-N-$\beta$-hydroxyethylaniline sulfate, a broad absorption peak in the spectral region of from about 700 to 850 nm was also observed. In repeating the above procedure with color developing agents 2,6-dimethyl-4-diethylaminoaniline and 4-amino-3-methyl-N,N-diethylaniline hydrochloride produced dye images having absorption peaks within the 750 to 850 nm range, but without any evidence of double peaking, that is, a broadening of the absorption peak throughout the 750 to 850 nm range.

EXAMPLE 3

The procedure of Example 2, paragraphs A, B and C, was repeated, but with the substitution of one of the coupler solvents indicated below in a concentration of 1.08 grams per square meter and a coupler to coupler solvent ratio of 1:1. A comparison of absorption characteristics is shown in FIG. 3.

Table IX

Figure 3:
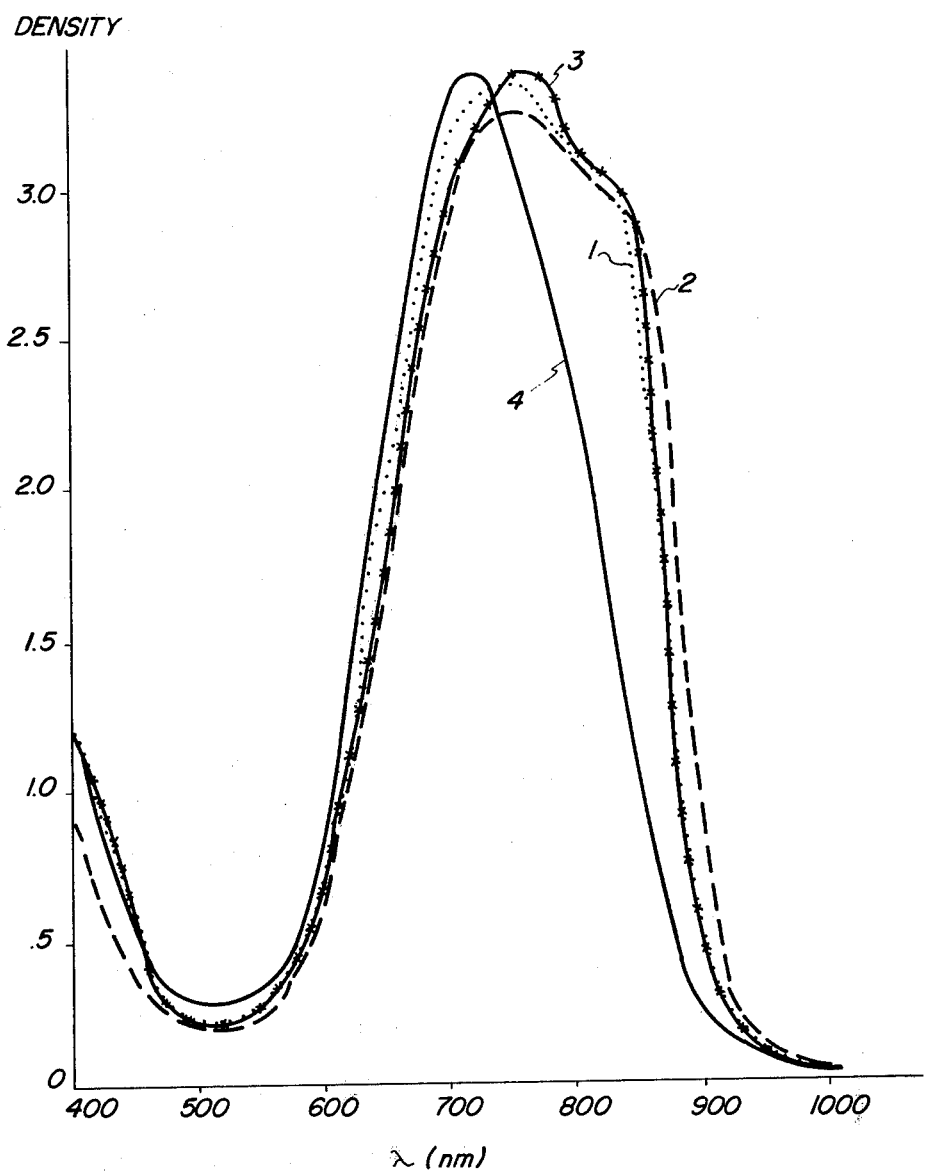

| Figure 3 Curve | Coupler Solvent |
|---|---|
| 1 | Di-n-butyl phthalate |
| 2 | 2,4-Di-tert-amylphenol |
| 3 | 2,4-Di-n-amylphenol |
| 4 | 4-Nonylphenol |

By reference to FIG. 3 it can be seen that the Curves 1, 2 and 3 exhibits a broad double-peak characteristic in the spectral region of from about 700 to 850 nm. By contrast Curve 4 does not exhibit a broad double-peak characteristic, but does produce a dye density of greater than 1 over the spectral region of from 750 to 850 nm.

EXAMPLE 4

The procedure of Example 1, paragraphs A, B and C, was repeated, but with the ratio of coupler to coupler solvent varied. The concentration of the coupler was in each instance held constant. The ratios of coupler to coupler solvent are correlated to the curves in FIG. 4 in Table X.

Table X

Figure 4:
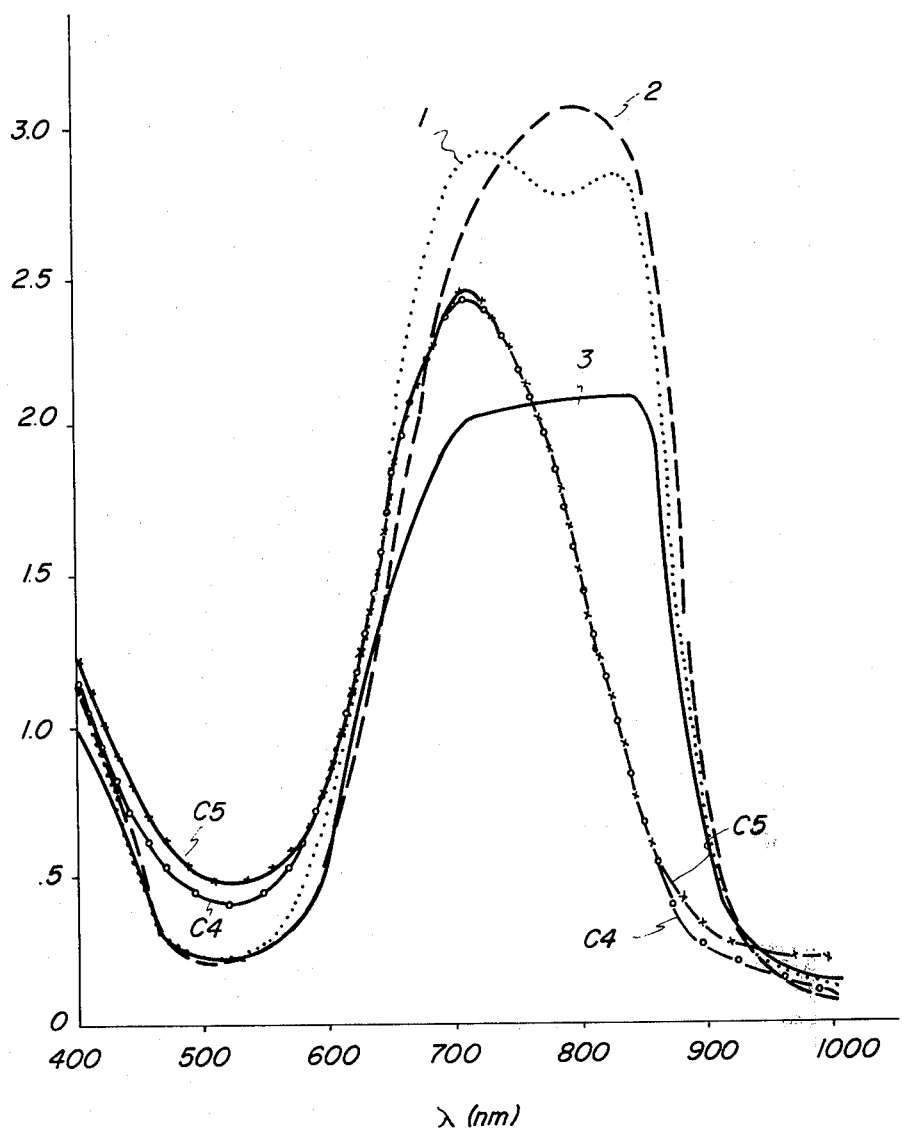

| Figure 4 Curve | Coupler:Coupler Solvent |
|---|---|
| 1 | 1:1 |
| 2 | 1:0.5 |
| 3 | 1:0.25 |
| C4 | 1:0.10 |
| C5 | 1:0 |

A distinct double peak characteristic is seen in Curves 1, 2 and 3. However, Curves C4 and C5 show an absorption peak in the range of about 725 nm with no double peak characteristic in evidence. These curves illustrate the importance of having a coupler solvent present to obtain the absorption characteristic desired. Although not shown in FIG. 4, when the ratio of coupler to coupler solvent was 1:2, a double peak characteristic was also observed.

EXAMPLE 5

A. A color motion picture print film (Eastman Color Print Film, type 7381) was overcoated with a sound track recording layer as set forth below in Table XI.

Table XI

| Sound Track Recording Layer |
|---|
| Gelatino-Silver Halide Emulsion Layer: Silver Chlorobromide sensitized to 485 nm (0.864); Gelatin (2.16); Coupler 1 (1.08); Coupler Solvent Di-n-butyl phthalate (0.54) |

An overcoat layer comprising 0.98 gram per square meter gelatin was then applied.

B. The resulting photographic element was then exposed to blue, green and red light in the picture areas of the film and exposed at 485 nm in the sound track areas following conventional procedures for exposing integral sound track motion picture film.

C. The photographic element was then processed at 27° C. according to the conventional procedure for Eastman Color Print Film, except that the only processing given the entire film was that normally applied to the picture recording areas and no separate processing was given to the sound track recording area. The following procedure was employed:

The element was rinsed for 10 seconds in a bath of the composition set forth in Table XII.

Table XII

| Prebath | |
|---|---|
| 800 ml | Water |
| 20 g | Borax |
| 100 g | Sodium sulfate |
| 1.0 g | NaOH |
| | Water to make 1 liter |

The element was then rinsed for 10 seconds in water and immersed for 5 minutes, 20 seconds in a color developer of the composition set forth in Table XIII.

Table XIII

| Color Developer | |
|---|---|
| 800 ml | Water |
| 2.0 g | Sodium hexametaphosphate |
| 4.0 g | Sodium sulfite |
| 3.0 g | 4-Amino-3-methyl-N,N-diethylaniline hydrochloride |
| 20.0 g | Sodium carbonate |
| 2.0 g | Potassium bromide |
| | Water to make 1 liter |

The element was then again rinsed for 10 seconds in water and immersed for 1 minute in a fix bath of the composition set forth in Table XIV.

Table XIV

| Fix Bath | |
|---|---|
| 600 ml | Water |
| 240 g | Sodium thiosulfate |
| 15 g | Sodium sulfite |
| 13.4 ml | Glacial Acetic Acid |
| 7.5 g | Boric acid |
| 15.0 g | Potassium Alum |
| | Water to make 1 liter |

The element was then washed for 40 seconds in water and immersed for 4 minutes in a bleach bath of the composition set forth in Table XV.

Table XV

| | Bleach Bath |
|---|---|
| 800 ml | Water |
| 20.0 g | Potassium bromide |
| 5.0 g | Potassium dichromate |
| 40.0 g | Potassium Alum |
| | Water to make 1 liter |

The element was again washed in water for 1 minute and then immersed in a second fix bath for 2 minutes identical in composition to that of Table XIV. The element was then washed again in water for 5 minutes and immersed for 10 minutes in a stabilizer bath of the composition set forth in Table XVI and then allowed to dry.

Table XVI

| | Stabilization Bath |
|---|---|
| 10-20 ml | 37% Formaldehyde Solution |
| 2 ml | Wetting Agent |
| | Water to make 1 liter |

D. The procedure of paragraphs A, B and C above was repeated with a second, identical photographic element, except that conventional processing for Eastman Color Print film was employed so that a silver sound track was left in the film. In a critical listening test, the infrared dye sound track produced in the first element and the silver sound track produced in the second, control element were found to be indistinguishable after the projector volume was adjusted to compensate for a 4.5 decibel loss in output of the infrared dye sound track image. The processing of the first element according to the invention was easier and simpler than processing the second, control element and this advantage was deemed to more than compensate for the minor disadvantage of a 4.5 decibel loss in sound output, since the projector volume could be readily turned up to compensate for this difference.

The invention has been described in detail with particular reference to preferred embodiments thereof, but it will be understood that variations and modifications can be effected within the spirit and scope of the invention.

What is claimed is:

1. In a silver halide photographic element comprising a support and, coated thereon, at least one layer unit which comprises a photographic silver halide emulsion layer and coupler solvent particles dispersed in a photographically useful amount in said emulsion layer or in an adjacent hydrophilic colloid layer, the improvement wherein said coupler solvent particles are comprised of a combination, capable of permitting the formation of a microcrystalline dye, of a coupler of the formula

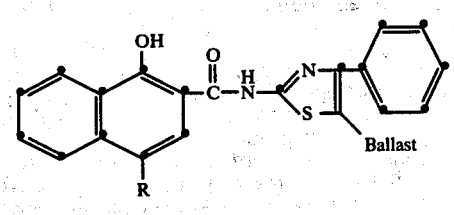

wherein
R is a coupling-off group and
Ballast is a hydrophobic photographic ballasting group and
a coupler solvent chosen from the group consisting of

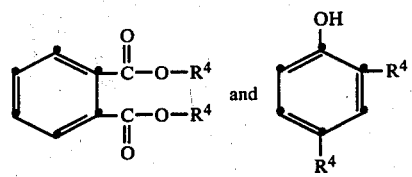

wherein $R^4$ is alkyl of from 1 to 6 carbon atoms;
said coupler and said coupler solvent being present in a weight ratio of from 5:1 to 1:2.

2. An improved photographic element according to claim 1 wherein said Ballast is an alkyl group of from 8 to 30 carbon atoms.

3. An improved photographic element according to claim 1 wherein said polar group $R^2$ is a hydroxy group or a carboxylic acid, salt or ester group.

4. An improved photographic element according to claim 1 wherein said coupler and said coupler solvent are present in a weight ratio of from 4:1 to 1:1.

5. An improved photographic element according to claim 1 wherein said silver halide emulsion layer is sensitized to the infrared portion of the spectrum.

6. An improved photographic element according to claim 1 wherein said silver halide emulsion layer is sensitized in the region of the spectrum from 470 to 500 nm.

7. An improved photographic element according to claim 1 wherein said element includes at least three layer units, one spectrally responsive to the blue region of the spectrum and containing a yellow dye-forming coupler, one spectrally responsive to the green region of the spectrum and containing a magenta dye-forming coupler and one spectrally responsive to the red region of the spectrum and containing a cyan dye-forming coupler.

8. An improved photographic element according to claim 1 wherein said coupler is present in a concentration sufficient to yield a dye density of at least 1 in the 800 nm region of the spectrum.

9. An improved photographic element according to claim 2 wherein said coupler is present in a concentration of from 0.40 to 1.30 grams per square meter.

10. A photographic element adapted to form a multicolor photographic image and an integral infrared absorbing dye sound track capable of producing a maximum density in excess of 1 throughout the spectral region of from 750 to 850 nm comprising
a transparent film support,
a first layer unit coated on said film support comprising a gelatino-silver halide emulsion layer having a peak sensitivity to a portion of the spectrum within the blue region at a wavelength shorter than 470 nm and containing a yellow dye-forming coupler,
a second layer unit coated over said first layer unit comprising a gelatino-silver halide emulsion layer having a peak sensitivity to the red portion of the spectrum and containing a cyan dye-forming coupler,
a third layer unit coated over said second layer unit comprising a gelatino-silver halide emulsion layer having a peak sensitivity to the green portion of the spectrum and containing a magenta dye-forming coupler, and a fourth layer unit coated over said third layer unit comprising a gelatino-silver halide emulsion layer having a peak sensitivity within the 470 to 500 nm region of the spectrum and containing coupler solvent particles comprised of a combination, capable of permitting the formation of a microcrystalline dye, of an infrared absorbing dye-forming coupler in a concentration of from 0.65 to 1.05 grams per square meter of the formula

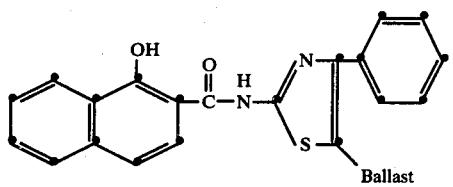

wherein Ballast is a straight-chain alkyl group of from 10 to 20 carbon atoms and a coupler solvent chosen from the group consisting of

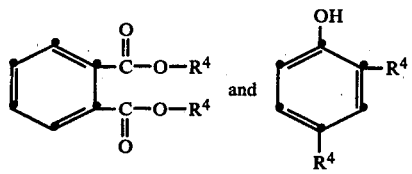

wherein $R^4$ is alkyl of from 1 to 6 carbon atoms, said coupler and said coupler solvent being present in said particles in a ratio of from 4:1 to 1:1.

11. A photographic element according to claim 10 wherein Ballast is a straight chain alkyl group from 12 to 16 carbon atoms, $R^4$ is butyl or amyl and the ratio of said infrared absorbing dye-forming coupler to said coupler solvent is from 2.5:1 to 1.5:1.

12. A composition which can be coated to form a layer of a photographic element comprising a hydrophilic colloid and coupler solvent particles dispersed therein in a photographically useful amount comprised of a combination, capable of permitting the formation of a microcrystalline dye, of a coupler of the formula

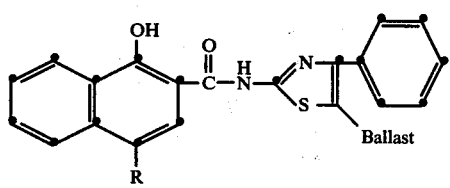

wherein

R is a coupling-off group and

Ballast is a hydrophobic photographic ballasting group and a coupler solvent is chosen from the group consisting of

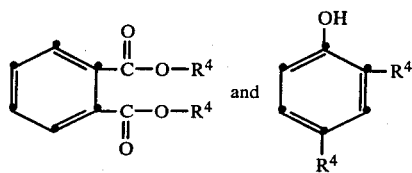

wherein $R^4$ is an alkyl group of from 1 to 6 carbon atoms; and said coupler and said solvent being present in a weight ratio of from 5:1 to 1:2.

13. A gelatino-silver halide emulsion which can be coated to form a layer of a photographic element comprising coupler solvent particles dispersed therein in a photographically useful amount comprised of a combination, capable of permitting the formation of a microcrystalline dye, of a coupler of the formula

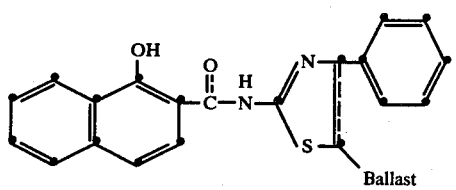

wherein Ballast is a straight-chain alkyl group of from 10 to 20 carbon atoms and a coupler solvent is chosen from the group consisting of

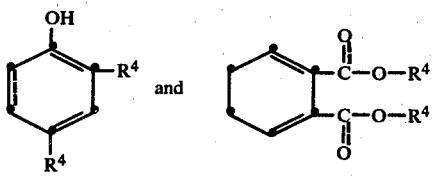

wherein $R^4$ is an alkyl group of from 1 to 6 carbon atoms;

said coupler and said coupler solvent is present in a weight ratio of from 4:1 to 1:1.

14. An improved silver halide emulsion according to claim 13 wherein said emulsion is spectrally sensitized to the infrared region of the spectrum.

15. An improved silver halide emulsion according to claim 13 wherein said emulsion is spectrally sensitized to have a peak sensitivity within the 470 to 500 nm region of the spectrum.

16. An improved silver halide emulsion according to claim 13 wherein Ballast is a straight-chain alkyl group of from 12 to 16 carbon atoms.

17. In a gelatino-silver halide emulsion which can be coated to form a layer of a photographic element comprising coupler solvent particles dispersed therein in a photographically useful amount comprised of a coupler and a coupler solvent, the improvement wherein said coupler is 1-hydroxy-N-(2-phenyl-3-tetradecylthiazolyl)-2-naphthamide;

said coupler solvent is chosen from the group consisting of dibutyl phthalate and 2,4-diamylphenol; and said coupler and said coupler solvent are present in a weight ratio of from 2.5:1 to 1.5:1.

18. An improved photographic element according to claim 1 wherein said coupling-off group is chosen from the class consisting of hydrogen and alkoxy, aryloxy, arylazo, thioether, oxazolyl, diazolyl, triazolyl and tetrazolyl coupling-off groups.

19. A composition according to claim 12 wherein said coupling-off group is chosen from the class consisting of hydrogen and alkoxy, aryloxy, arylazo, thioether, oxazolyl, diazolyl, triazolyl and tetrazolyl coupling-off groups.

* * * * *